US007666676B2

(12) United States Patent
Lawman et al.

(10) Patent No.: US 7,666,676 B2
(45) Date of Patent: Feb. 23, 2010

(54) MODULATING CANCER CELL CHARACTERISTICS

(75) Inventors: Michael J. P. Lawman, Tampa, FL (US); Selena Braccili, Tampa, FL (US)

(73) Assignee: St. Joseph's Children's Hospital, Tampa, FL (US)

( * ) Notice: Subject to any disclaimer, the term of this patent is extended or adjusted under 35 U.S.C. 154(b) by 68 days.

(21) Appl. No.: 11/436,962

(22) Filed: May 16, 2006

(65) Prior Publication Data

US 2007/0161588 A1 Jul. 12, 2007

Related U.S. Application Data

(60) Provisional application No. 60/681,366, filed on May 16, 2005.

(51) Int. Cl.
*C12N 15/00* (2006.01)
*C12N 5/00* (2006.01)
*C07H 21/04* (2006.01)
(52) U.S. Cl. .................. 435/440; 435/325; 536/24.5
(58) Field of Classification Search ................ 435/325, 435/440; 536/24.5
See application file for complete search history.

(56) References Cited

U.S. PATENT DOCUMENTS 5,883,124 A * 3/1999 Samid ..................... 514/538
2004/0072345 A1* 4/2004 Altaba et al. ............. 435/368

OTHER PUBLICATIONS

Ambion, 2 pages (http://www.ambion.com/techlib/misc/siRNA_finder.html) accessed Sep. 27, 2007, available to the public 2002.*
Tuschl (Molecular Interventions, 2002; vol. 2(3), pp. 158-167).*
Hallahan et al. (Cancer Research, 2004, vol. 64, pp. 7794-7800).*
Jarov, A et al Developmental Biology, 2003; vol. 261, pp. 520-536.*
Bedford, J.S., et al. "Applications of RNA interference for studies in DNA damage processing, genome stability, mutagenesis, and cancer", *Seminars in Cancer Biology*. Apr. 28, 2003; pp. 301-308, vol. 13 No. 4.
Bertrand, Jr, J.R., et al. "Comparison of antisense oligonucleotides and siRNAs in cell culture and in vivo". *Biochemical and Biophysical Research Communications*. Aug. 2, 2002; pp. 1000-1004, vol. 296 No. 4.
Borkhardt A. "Blocking oncogenes in malignant cells by RNA interference—new hope for a highly specific cancer treatment?" *Cancer Cell*. Sep. 2002; pp. 167-168, vol. 2 No. 3.
Brummelkamp, T.R., et al. "A system for stable expression of short interfering RNAs in mammalian cells". *Science*. Apr. 19, 2002; pp. 550-553, vol. 296.
Buckingham, S.D., et al. "RNA interference: from model organisms towards therapy for neural and neuromuscular disorders". *Human Molecular Genetics*. Jul. 19, 2004; pp. R275-R288, vol. 13 No. 2.

Caplen, N.J., et al. "Short interfering RNA (siRNA)-mediated RNA interference (RNAi) in human cells". *Ann NY Academy of Sciences*, Dec. 2003; pp. 56-62, vol. 1002.
Clayton, J. "RNA interference: the silent treatment". *Nature*. Sep. 30, 2004; pp. 599-605, vol. 431, No. 7008.
Damm-Welk, C., et al. "Targeting oncogenic fusion genes in leukemias and lymphomas by RNA interference", *Seminars in Cancer Biology*, Aug. 2003; pp. 283-292. vol. 13 No. 4.
Dave, R.S., et al. "RNA interference: on the road to an alternate therapeutic strategy!" *Reviews in Medical Virology*. Nov.-Dec. 2003; pp. 373-385, vol. 13 No. 6.
Davidson, B.L., et al. "Molecular medicine for the brain: silencing of disease genes with RNA interference". *Lancet Neurology*. Mar. 2004; pp. 145-149, vol. 3 No. 3.
Deveraux, Q.L., et al. "Exposing oncogenic dependencies for cancer drug target discovery and validation using RNAi". *Seminars in Cancer Biology*. Aug. 2003; pp. 293-300, vol. 13 No. 4.
Dudley, N.R., et al. "RNA interference: silencing in the cytoplasm and nucleus", *Current Opinion in Molecular Therapeutics*. Apr. 2003; pp. 113-117, vol. 5 No. 2.
Duursma, A.M., et al. "Ras interference as cancer therapy". *Seminars in Cancer Biology*. Aug. 2003; pp. 267- 273, vol. 13 No. 4.
Duxbury, M.S. et al. "Systemic siRNA-mediated gene silencing: a new approach to targeted therapy of cancer". *Annals of Surgery*. Oct. 2004; pp. 667-674, vol. 240 No. 4.
Elbashir, S.M., et al. "Duplexes of 21-nucleotide RNAs mediate RNA interference in cultured mammalian cells". *Nature*. May 24, 2001; pp. 494-498, vol. 411.
Fan, X., et al. "Notch1 and Notch2 Have Opposite Effects on Embryonal Brain Tumor Growth". *Cancer Research*. Nov. 1, 2004; pp. 7787-7793, vol. 64.
Gitlin, L., et al. "Nucleic acid-based immune system: the antiviral potential of mammalian RNA silencing". *Journal of Virology*. Jul. 2003; pp. 7159-7165, vol. 77 No. 13.
Gottesman, S. "Stealth regulation: biological circuits with small RNA switches". *Genes & Development*. Nov. 15, 2002; pp. 2829-2842, vol. 16 No. 22.
Hamilton, A., et al. "Two classes of short interfering RNA in RNA silencing". *EMBO Journal*. Sep. 2, 2002; pp. 4671-4679, vol. 21 No. 17.
Hannon, G,J., "RNA interference". *Nature*. Jul. 11, 2002; pp. 244-251, vol. 418 No. 6894.
Harborth, J., et al. "Identification of essential genes in cultured mammalian cells using small interfering RNAs". *Journal of Cell Science*. 2001; pp. 4557-4565, vol. 114.
Hemann, M.T., et al. "An epi-allelic series of p53 hypomorphs created by stable RNAi produces distinct tumor phenotypes in vivo". *Nat Genet*. Mar. 2003; pp. 396-400, vol. 33 No. 3.

(Continued)

*Primary Examiner*—J. E Angell
(74) *Attorney, Agent, or Firm*—Saliwanchik, LLoyd & Saliwanchik (57) ABSTRACT

The hedgehog pathway in cerebellar cancer cells was modulated with siRNA specifically targeted to the shh and gli-I genes. Silencing of the two genes in a medullablastoma cell line transfected with the siRNAs caused significant reduction of mRNA specific for the targeted shh and gli-I genes and a loss of protein expression. The disclosed methods and compositions may be useful for treatment of a range of primitive neuroectodermal tumors (PNET) by shutting down or modulating the expression of gene products associated with the hedgehog pathway.

5 Claims, 8 Drawing Sheets

OTHER PUBLICATIONS

Hommel, J.D. et al. "Local gene knockdown in the brain using viral-mediated RNA interference". *Nature Medicine*. Dec. 2003; pp. 1539-1544, vol. 9 No. 12.

Hutvagner, G., et al. "RNAi: Nature abhors a double-strand". *Current Opinion in Genetics & Development*. 2002; pp. 225-232, vol. 12.

Jiang, Z., et al. "Lovastatin-induced up-regulation of the BH3-only protein, Bim, and cell death in glioblastoma cells". *Journal of Neurochemistry*. 2004; pp. 168-178, vol. 89 No. 1.

Jones, S.W., et al. "siRNA for gene silencing: a route to drug target discovery". *Current Opinion in Pharmacology*, Aug. 17, 2004; pp. 522-527. vol. 4 No. 5.

Kittler, R., et al. "RNA interference: gene silencing in the fast lane". *Seminars in Cancer Biology*. Aug. 2003; pp. 259-265, vol. 13 No. 4.

Krichevsky, A.M., et al. "RNAi functions in cultured mammalian neurons". *Proceedings of the National Academy of Sciences of the United States of America*. Sep. 3, 2002; pp. 11926-9, vol. 99 No. 18.

Lapteva, N., et al. "CXCR4 knockdown by small interfering RNA abrogates breast tumor growth in vivo". *Cancer Gene Therapy*. 2005; pp. 84-89, vol. 12.

Lavery, K.S., et al. "Antisense and RNAi: powerful tools in drug target discovery and validation". Curr Opin Drug Discov Devel. Jul. 2003; pp. 561-569, vol. 6 No. 4.

Lu, P.Y., et al. "siRNA-mediated antitumorigenesis for drug target validation and therapeutics". *Curr Opin Mol Ther*. Jun. 2003; pp. 225-234, vol. 5 No. 3.

McCaffrey, A.P., et al. "RNA interference in adult mice". *Nature*. Jul. 4, 2002; pp. 38-39, vol. 418.

McManus, M.T., etal. "Gene silencing in mammals by small interfering RNAs". *Nat Rev Genet*. Oct. 2002; pp. 737-747, vol. 3 No. 10.

Meister, G., et al. "Mechanisms of gene silencing by double-stranded RNA". *Nature*. Sep. 16, 2004; pp. 343-349, vol. 431 No. 7006.

Mello, C.C., et al. "Revealing the world of RNA interference". *Nature*. Sep. 16, 2004; pp. 338-342, vol. 431 No. 7006.

Milhavet, O., et al. "RNA interference in biology and medicine". *Pharmacological Review*. Dec. 2003; pp. 629-648, vol. 55 No. 4.

Ning, S., et al. "siRNA-mediated down-regulation of survivin inhibits bladder cancer cell growth". *International Journal of Oncology*. 2004; pp. 1065-1071, vol. 25 No. 4.

Paddison, P.J., et al. "Short hairpin RNAs (shRNAs) induce sequence-specific silencing in mammalian cells". *Genes & Development*. 2002; pp. 948-958, vol. 16.

Paddison, P.J., et al. "Stable suppression of gene expression by RNAi in mammalian cells". *Proceedings of the National Academy of Sciences of the United States of America*, Jan. 29, 2002; pp. 1443-1448, vol. 99 No. 3.

Paddison, P.J., et al. "RNA interference: the new somatic cell genetics?" *Cancer Cell*. Jul. 2002; pp. 17-23, vol. 2 No. 1.

Paddison PJ, et al. "siRNAs and shRNAs: skeleton keys to the human genome". *Curr Opin Mol Ther*. Jun. 2003; pp. 217-224, vol. 5 No. 3.

Pickford AS, et al. "RNA-mediated gene silencing". *Cellular and Molecular Life Sciences*, May 2003; pp. 871-882, vol. 60 No. 5.

Plasterk, R.H.A. "RNA silencing: The genome's immune system". *Science*. May 17, 2002; pp. 1263-1265, vol. 296.

Raab, R.M., et al. "Dynamics of gene silencing by RNA interference". *Biotechnology and Bioengineering*. Oct. 5, 2004; pp. 121-132, vol. 88 No. 1.

Saunders, L.R., et al. "The dsRNA binding protein family: critical roles, diverse cellular functions". *FASEB Journal*. Jun. 2003; pp. 961-983, vol. 17 No. 9.

Scherr, M., et al. "Gene silencing mediated by small interfering RNAs in mammalian cells". *Current Medicinal Chemistry*. Feb. 2003; pp. 245-256, vol. 10 No. 3.

Sheng, T., et al. "Activation of the hedgehog pathway in advanced prostate cancer". *Molecular Cancer*. Oct. 13, 2004, vol. 3. No. 29.

Shi, Y. "Mammalian RNAi for the masses". *Trends Genet*. Jan. 2003; pp. 9-12, vol. 19 No. 1.

Sioud, M., "Therapeutic siRNAs". *Trends in Pharmacological Sciences*. Jan. 2004; pp. 22-28, vol. 25 No. 1.

Sorensen, D.R., et al. "Gene silencing by systemic delivery of synthetic siRNAs in adult mice". *Journal of Molecular Biology*. Apr. 4, 2003; pp. 761-766, vol. 327 No. 4.

Stecca, B., et al. "The therapeutic potential of modulators of the Hedgehog-Gil signaling pathway". *Journal of Biology*. Nov. 6, 2002; vol. 1, No. 2, Article 9.

Timmons. L. "The long and short of siRNAs". *Molecular Cell*, Sep. 2002; pp. 435-437, vol. 10 No. 3.

Tuschl, T. "Expanding small RNA interference". *Nature Biotechnology*. May 2002; pp. 446-468, vol. 20.

Verma, N.K., et al. "RNA-mediated gene silencing: mechanisms and its therapeutic applications". *Journal of Clinical Pharmacy Therapeutics*, 2004; pp. 395-404, vol. 29 No. 5.

Wal,L N.R., at al. "Small RNA: can RNA interference be exploited for therapy?" *Lancet*. Oct. 25, 2003; pp. 1401-1403; vol. 362 No. 9393.

Wang, J., at al. "Dysregulated Sonic hedgehog signaling and medulloblastoma consequent to IFN-α-stimulated STAT2-independent production of IFN-γ in the brain". *Journal of Clinical Investigation*. Aug. 2003; pp. 535-543, vol. 112.

Wilson, J.A., et al. "Induction of RNA interference using short interfering RNA expression vectors in cell culture and animal systems". *Curr Opin Mol Ther*. Aug. 2003; pp. 389-396, vol. 5 No. 4.

Wood, M.J., et al. "Ribozymes and siRNA for the treatment of diseases of the nervous system". *Curr Opin Mol Ther*. Aug. 2003; pp. 383-388, vol. 5 No. 4.

Xia, H., et al. "siRNA-mediated gene silencing in vitro and in vivo". *Nature Biotechnology*. Oct. 2002; pp. 1006-1010, vol. 20 No. 10.

Zamore, P.D., "Ancient pathways programmed by small RNAs". *Science*. May 17, 2002; pp. 1265-1269, vol. 296.

* cited by examiner

Figure 3: Representative gels of the in vitro Synthesized anti-sense probes

**Figure 4A: Determination of the Potential 19mers for the Synthesis of the Anti-sense *Gli1*-RNA Target Sequence**

```
                    Gli1 Target Sequences:
#1
SiRNA #1 (%GC = 29 & annealed MW = 13240.4)
5'                              3'
GGAGAAAUUUGAUAAAUGACtt    Sense      (SEQ ID NO: 1)

5'                              3'
GUCAUUAUCAAAUUUCUCCtt     Antisense  (SEQ ID NO: 2)

#2
SiRNA #2 (%GC = 48 & annealed MW = 13300.4)
5'                              3'
GGGCCCACUCUUUUCUUCUtt     Sense      (SEQ ID NO: 3)

5'                              3'
AGAAGAAAAGAGUGGGCCCtt     Antisense  (SEQ ID NO: 4)
```

**Figure 4B: Determination of the Potential 19mers for the Synthesis of the Anti-sense *SHh*-RNA Target Sequence**

```
                    SHh Target Sequences:
#1
SiRNA #1 (%GC = 43 & annealed MW = 13300.4)
5'                              3'
GGAUGAAGAAAACACCGGAtt     Sense      (SEQ ID NO: 5)

5'                              3'
UCCGGUGUUUUCUUCAUCCtt     Antisense  (SEQ ID NO: 6)

#2
SiRNA#2 (%GC = 43 & annealed MW = 13300.4)
5'                              3'
GGUAUGAAGGGAAGAUCUCtt     Sense      (SEQ ID NO: 7)

5'                              3'
GAGAUCUUCCCUUCAUACCtt     Antisense  (SEQ ID NO: 8)
```

**Figure 4C: Determination of the Potential 19mers for the Synthesis of the Anti-sense *βact*-RNA Target Sequence**

```
                    ACTB Target sequences:
#1
SiRNA #1 (%GC = 38 & annealed MW = 13270.4)
5'                              3'
GGACUUUGAUUGCACAUUGtt     Sense      (SEQ ID NO: 9)

5'                              3'
CAAUGUGCAAUCAAAGUCCtc     Antisense  (SEQ ID NO: 10)

#2
SiRNA #2 (%GC = 52 & annealed MW = 13330.4)
5'                              3'
GGAUUCCUAUGUGGGCGACtt     Sense      (SEQ ID NO: 11)

5'                              3'
GUCGCCCACAUAGGAAUCCtt     Antisense  (SEQ ID NO: 12)
```

Figure 5: Northern Blot Using the SHh & Gli1 *In Vitro* Synthesized Probes

MODULATING CANCER CELL CHARACTERISTICS

CROSS-REFERENCE TO A RELATED APPLICATION

This application claims the benefit of U.S. provisional application Ser. No. 60/681,366, filed May 16, 2005, in its entirety, including all figures, tables, and sequences.

FIELD OF THE INVENTION

The invention relates generally to the fields of biology, medicine, pediatrics, and oncology. More particularly, the invention relates to composition and methods for modulating the characteristics of cerebellar cancer cells.

BACKGROUND

Pediatric brain tumors are the third most frequent malignancy of children, and brain tumors are the leading cause of death in children with cancer. Medulloblastoma is the most common pediatric tumor of the cerebellum. These tumors can seed along the neuraxis and metastasize to extraneural tissue. During brain development, embryonic neuroepithelial cells migrate outwards and laterally to form the external granular layer of the cerebellum. Primitive neuroectodermal tumors (PNET), like medulloblastomas and basal cell carcinomas (BCC) of the skin, have been associated with two inherited cancer syndromes: Gorlin's and Turcot's. Gorlin's Syndrome, also called nevoid basal cell carcinoma syndrome (NBCCS), is an autosomal-dominant disease characterized by a range of tumor types such as BCC, medulloblastoma, ovarian fibroma, meningioma, fibrosarcoma, rhabdomyosarcoma and cardiac fibroma. Three percent of patients with Gorlin's develop medulloblastoma and Turcot patients are 92-fold more likely to develop medulloblastoma than the general population.

There is accumulating evidence that medulloblastomas result from the molecular dysregulation of the hedgehog (Hh) pathway, in particular sonic hedgehog (SHh), smoothen (Smo), patched (Ptch) and the transcription factor family, Gli1-3. The hh family of genes and their control in mammalian embryonic development is certainly pivotal. SHh plays a number of significant roles in embryonic development including the development of the cerebellum. SHh is produced by Purkinje cells and by granule neuron progenitor cells and is a mitogenic factor for granule neurons as well as a differentiation factor for Bergmann glial cells. In fact, cerebellum hyperproliferation appears to be the result of increased levels of SHh and its prolonged expression. Indeed, SHh has been shown to be associated with medulloblastomas from studies involving transgenic mice that over express SHh and in a transgenic human tissue model.

It is also known that mutations in ptch are responsible for Gorlin's Syndrome. In these individuals, one copy of the ptch gene is mutated, resulting in many of the heterozygous cases of medulloblastoma. Between 12 and 40% of non-inherited BCC arise from inactivation of both alleles of ptch. Ptch mutations, along with several other members of the Hh signaling pathway, also have been directly implicated in the development of medulloblastomas.

Cubis interruptus (Ci) is the terminal component of the Hh pathway, mediating transcriptional activation of hh target genes in response to Hh. Binding sites for Ci have been identified upstream to the promoters of both wg and ptch. There is a high degree of sequence homology between ci and the vertebrate Gli family of transcription factors. In vertebrates there are three homologs of the ci gene: gli1, gli2 and gli3, each having its own distinct pattern of expression. The Gli proteins are large transcription factors that bind DNA in a sequence specific manner via the last three fingers of their five zinc-finger domain. Gli1 is the most potent activator. Gli2 & 3 are thought to have dual functions both as a modified full-length activator and as a truncated processed repressor. Gli1 is constitutively activated in BCC, NBCCS and medulloblastoma.

Since its discovery in plants, post-transcriptional gene silencing has become an important tool in molecular biology. It was shown early on that gene silencing was mediated through a diffusable trans-acting product and later that this trans-acting factor was double-stranded RNA (dsRNA). Both antisense and sense RNA were able to shut down expression of a target gene. Gene silencing studies have shown that dsRNA are more effective at suppressing target genes than anti-sense or sense-strands alone. Only a few molecules of dsRNA are required to attain complete gene silencing. This dsRNA effect has been termed RNA interference (RNAi). RNAi can also be induced by transfecting cells with plasmids that express siRNAs. Furthermore, plasmids containing a sequence encoding a hairpin-forming, 45-50mer double-stranded RNA molecule termed small hairpin RNA (shRNA) under the control of an RNA Polymerase III (Pol 111) promoter when transfected into mammalian cells, have been shown to be more stably expressed, more efficient at reducing the levels of both exogenous and endogenous gene products and provide longer term reduction in target gene than siRNAs alone.

Many researchers are now using RNAi as a tool to ascertain the function of genes because it allows one to create 'loss-of-function' phenotypes quickly and easily. RNAi may also hold promise as a gene-specific therapeutic for the treatment of infectious diseases and cancer.

SUMMARY

The invention relates to the discovery that siRNA-mediated silencing of the shh gene in medulloblastoma cells appeared to alter the phenotype, growth rate and growth characteristics of these cells. Accordingly, the invention features compositions and methods of modulating the phenotype of a cerebellar cancer cell by modulating expression of gene encoding a gene product involved in the hedgehog pathway.

Unless otherwise defined, all technical and legal terms used herein have the same meaning as commonly understood by one of ordinary skill in the art to which this invention belongs. Although methods and materials similar or equivalent to those described herein can be used in the practice or testing of the present invention, suitable methods and materials are described below. All patent applications mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

BRIEF DESCRIPTION OF THE SEQUENCES

SEQ ID NO:1 shows the nucleotide sequence of the sense strand of Gli1 target sequence #1 (SiRNA #1 (% GC=29 & annealed MW=13240.4)).

SEQ ID NO:2 shows the nucleotide sequence of the anti-sense strand of Gli1 target sequence #1 (SiRNA #1 (% GC=29 & annealed MW=13240.4)).

SEQ ID NO:3 shows the nucleotide sequence of the sense strand of Gli1 target sequence #2 (SiRNA #2 (% GC=48 & annealed MW=13300.4)).

SEQ ID NO:4 shows the nucleotide sequence of the anti-sense strand of Gli1 target sequence #2 (SiRNA #2 (% GC=48 & annealed MW=13300.4)).

SEQ ID NO:5 shows the nucleotide sequence of the sense strand of SHh target sequence #1 (SiRNA #1 (% GC=43 & annealed MW=13300.4)).

SEQ ID NO:6 shows the nucleotide sequence of the anti-sense strand of SHh target sequence #1 (SiRNA #1 (% GC 43 & annealed MW=13300.4)).

SEQ ID NO:7 shows the nucleotide sequence of the sense strand of SHh target sequence #2 (SiRNA#2 (% GC=43 & annealed MW=13300.4)).

SEQ ID NO:8 shows the nucleotide sequence of the anti-sense strand of SHh target sequence #2 (SiRNA#2 (% GC=43 & annealed MW=13300.4)).

SEQ ID NO:9 shows the nucleotide sequence of the sense strand of ACTB target sequence #1 (SiRNA #1 (% GC=38 & annealed MW=13270.4)).

SEQ ID NO:10 shows the nucleotide sequence of the anti-sense strand of ACTB target sequence #1 (SiRNA #1 (% GC=38 & annealed MW=13270.4)).

SEQ ID NO:11 shows the nucleotide sequence of the sense strand of ACTB target sequence #2 (SiRNA #1 (% GC=52 & annealed MW=13330.4)).

SEQ ID NO:12 shows the nucleotide sequence of the anti-sense strand of ACTB target sequence #2 (SiRNA #1 (% GC=52 & annealed MW=13330.4)).

DETAILED DESCRIPTION

Multiple siRNAs complementary to shh, gli-1 were evaluated to determine optimal methods for measuring siRNA-induced gene suppression. Multiple siRNAs complementary to the β-actin gene were used as a control. Two siRNAs were prepared for each target gene. These siRNA were transfected into a medulloblastoma cell line using Ambion's Silencer™ siRNA transfection kit. The effect of in vitro RNAi treatment of medulloblastoma cells on protein expression was measured using flow cytometry and western blot analysis. Alteration of mRNA levels following treatment was assessed using northern blot analysis. The results of these studies show that shh and gli-1 siRNA specifically targeted the mRNA for both shh and gli-1 genes which resulted in a significant decrease (greater than 90% by 96 hours following transfection) in the levels of targeted mRNAs and 85% protein expression as measured by western blot analysis. The loss of protein expression as measured by flow cytometry also showed that there was a significant decrease in the level of protein expression and a reduction in the number of cells expressing the proteins over the 96 hour period. The ability to silence the shh gene using siRNA appeared to alter the phenotype, growth rate and growth characteristics of the tumor cells in vitro. However, despite the silencing of the gli-1 gene, there was no apparent change in cell proliferation, growth characteristics or phenotype of the siRNA-treated tumor cells.

Materials and Methods

PNET cell cultures: Cells were routinely maintained in IMDM supplemented with 10% FBS and 0.6% L-glutamine. Cultures were incubated at 37° C. in T75 cm$^2$ plastic culture flasks in a humidified atmosphere of 5% $CO_2$ in air.

Phenotypic analysis of PNET cell cultures: PNET cell cultures were subjected to both flow cytometric analysis and indirect fluorescent antibody assays for the expression of Heat stable antigen (HSA), Vimentin, Synaptophysin, neurofibrillary protein-70 (NFP-70), neurofibrillary protein-250 (NFP-250), Nestin, glutamine synthetase, neuron-specific enolase (NSE) and neuroectodermal antigen (UJ13A), glial fibrillary acidic protein (GFAP) and for S-100. All the antibodies listed above were purchased from Chemcon International (Temecula, Calif.). The antibodies detecting SHh and Gli1antigens were purchased from ATCC (Rockville, Md.) and abcam (Cambridge, Mass.) respectively.

Flow cytometry: Cells were labeled as described below (Indirect fluorescent antibody [IFA] assays), placed in sheath fluid and analyzed on a FACSCalibur four-color flow cytometer (Becton Dickinson Immunocytometry Systems, CA) Data analysis was performed by using CellQuest Pro Data Analysing Software (Becton Dickinson Immunocytometry Systems, CA). The flow cytometer was calibrated prior to each run. Compensation was set up for FITC using single-stained cell populations. All cell analysis was carried out within a low orthogonal light scatter and forward light scatter windows at a rate of more than $2\times10^3$ cells sec-$^1$ Indirect fluorescent antibody (IFA) assays: All IFA experiments for the detection of both intracellular and extracellular antigens were conducted using CALTAG labs (Burlingame, Calif.) permeabilization kit. The procedure was as directed by the manufactures instructions. Briefly, for each cell sample to be analyzed an appropriate concentration of primary antibody was added to $1\times10^6$ cells. The cells were vortexed and incubated for 15 minutes at room temperature. Following this step, 100 ul of the fixing reagent was added and the cells incubated for a further 15 minutes at room temperature. Following incubation, the cells were washed once in 3 ml of phosphate buffered saline (PBS) supplemented with 5% FBS, centrifuged and the wash fluid removed. To the cell pellet, 100 ul of the permeabilization reagent and 10 ul of the FITC-labeled secondary antibody (anti mouse IgG) was added. The cells were vortexed and incubated at room temperature for 20 minutes. Following incubation the cells were washed as previously described above and either examined for fluorescence using UV microscopy or placed in sheath fluid for flow cytometric analysis.

Synthesis of siRNA for gene silencing: In the development of systems to measure gene silencing in mammalian cells, it appears that the most potent siRNAs are those that contain a 19 nucleotide complementary region between both strands (sense and antisense) plus a 2 nucleotide overhang at the 3' end.

The selection of siRNA target sites on the genes of interest started at the AUG start codon and the transcript scanned downstream for AA di-nucleotide sequences. All the AA di-nucleotide and the 3' adjacent 19 nucleotides were recorded. All the potential target sites were then compared to an appropriate genome database, such as BLAST for the mouse and human, for the elimination of those sequences that have significant homology to other coding sequences. The resulting target sequences were sent to Ambion, Inc. (Austin, Tex.) and complementary pairs of siRNA oligonucleotides with dTdT or UU 3' overhangs were synthesized. SiRNA's were synthesized for the genes encoding SHh and Gli1 and also for the reporter gene encoding beta-actin.

mRNA Isolation: PNET cells used for both total RNA and mRNA were grown as previously described. The isolation of and subsequent purification of PolyA mRNA was carried out using Qiagen's Oligotex Direct mRNA Kit (QIAGEN, Calif.) according to manufacturer's instructions.

Plasmid preparation: Cultures of *E. coli* containing plasmids (pT7pT3) with either Shh or Gli1 inserts were grown overnight at 37° C. in LB broth (with 50 ug/ml of ampicillin) in an orbital shaker. Purified plasmid preparations were prepared using Qiagen's QIAprep Spin Miniprep Kit (Qiagen, Calif.) according to manufacturer's instructions. Plasmid linearization was achieved with NotI (Promega Corporation).

Probe synthesis: Linearized plasmid DNA from the above digests was used to generate T7 RNA polymerase probes by in vitro transcription using Ambion's Strip-EZ™ RNA Kit (Ambion, Austin, Tex.) and following the procedure recommended by the manufacturer (Ambion, Austin, Tex.). Briefly, the reaction was set up in a 1.5 ml microcentrifuge tube at room temperature. The following components were added in order; 12 µl of nuclease-free water, 12 µl of template DNA from restriction digests, 4 µl of 10× Transcription Buffer, 2 µl of ATP Solution, 2 µl of Modified CTP Solution, 2 µl of GTP Solution, 2 µl of UTP Solution and 4 µl of T7 Enzyme Mix. Reactions incubated for 90 minutes at 40° C. After incubation, the DNA template was removed by adding 1 µl of DNase 1 and placing the reaction at 37° C. for 15 minutes. The reactions were stopped with 1 µl of 0.5M EDTA (Gibco BRL®) incubated at 75° C. for five minutes. Probes were then labeled using Ambion's BrightStar™ Psoralen-Biotin Kit. 30 µl of each probe was denatured at 100° C. for 10 minutes. The probes were then quick chilled in an ethanol/ice bath and placed in a 96 well plate that sat on an ice bath. 3 µl of Psoralen-Biotin was mixed with each probe and irradiated for 45 minutes under an ultraviolet 365 nm light. Each probe was diluted in 70 µl of TE Buffer. Non-crosslinked psoralen-biotin was removed by butanol extraction. One extraction/probe was done using 200 µof Water Saturated n-butanol followed by centrifugation and removal of the butanol layer. All probes were then stored at −70° C.

Northern blot analysis: The size and abundance of mRNA was determined by northern blot analysis. All procedures were carried out using Ambion's NorthernMax™-Gly Kit (Ambion, Austin Tex.). Detection of signal was determined using Ambion's BrightStar™ BioDectect™ Kit. Exposure was done for 4-6 hours on Hyperfilm™ ECL (Amersham Biosciences).

Characterization of the siRNA induced gene silencing of target genes: Two target sequences per gene from the 5', 3' ends and medial regions were selected based upon the predicted sequence as reported in 'Ensembl Human Genome Browser' (GeneView). For transfection, the different populations of PNET tumor cells were grown to between 40-70% confluency in T75 $cm^2$ tissue culture flasks in normal IMDM growth media. The individual siRNAs, at varying concentrations, including transfection reagent, either siPORT™ Amine (a polyamine) or siPORT™ Lipid (a mixture of cationic and neutral lipids), and Opti-MEM were mixed and incubated together at room temperature for 15-20 minutes. Following incubation, the siRNA mixture was added to the cell cultures and incubated for up to 96 hours. At varying time intervals, the tumor cells were harvested for analysis of both specific mRNA (northern blot) and protein (western blot and flow cytometry). Targeted cells were also examined for alterations in phenotype, growth characteristics and for in vivo tumorogenicity.

Results

Figure 1:
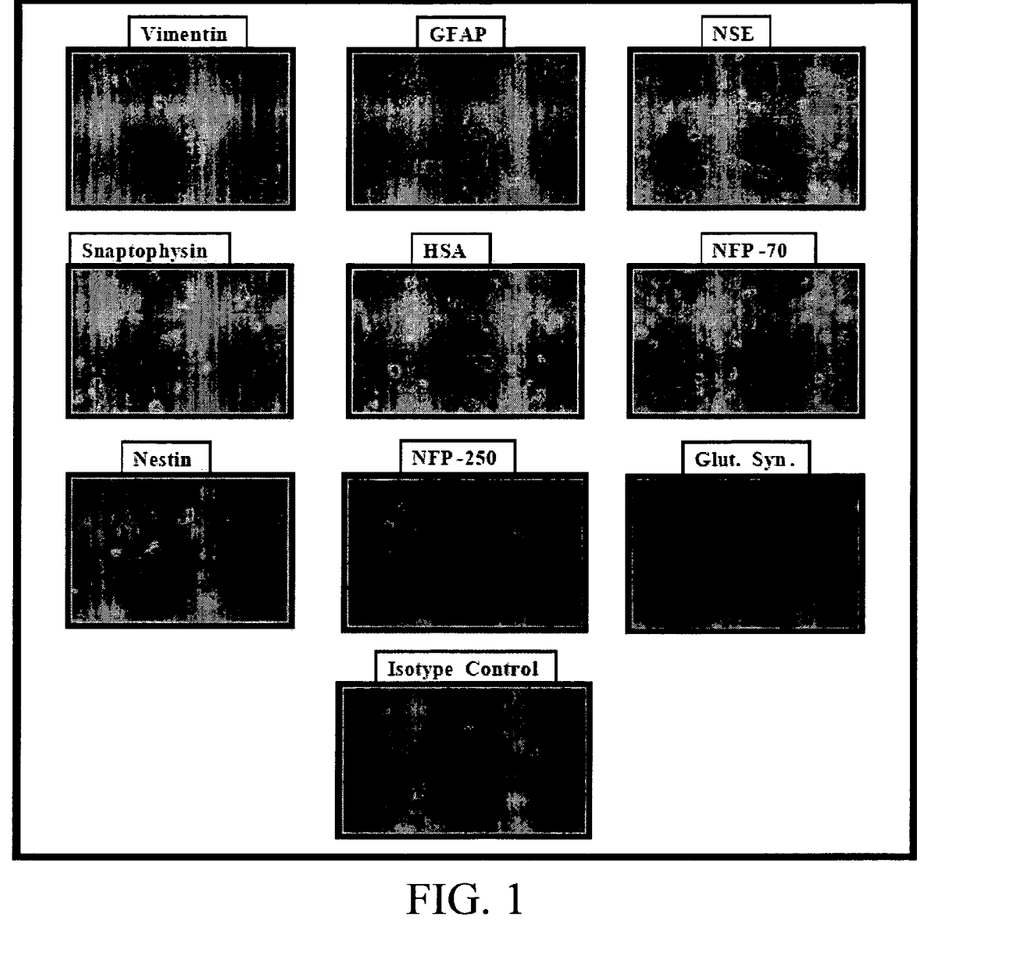
FIG. 1 is series of micrographs showing expression of neural markers by tumor cells.
Figure 2A:
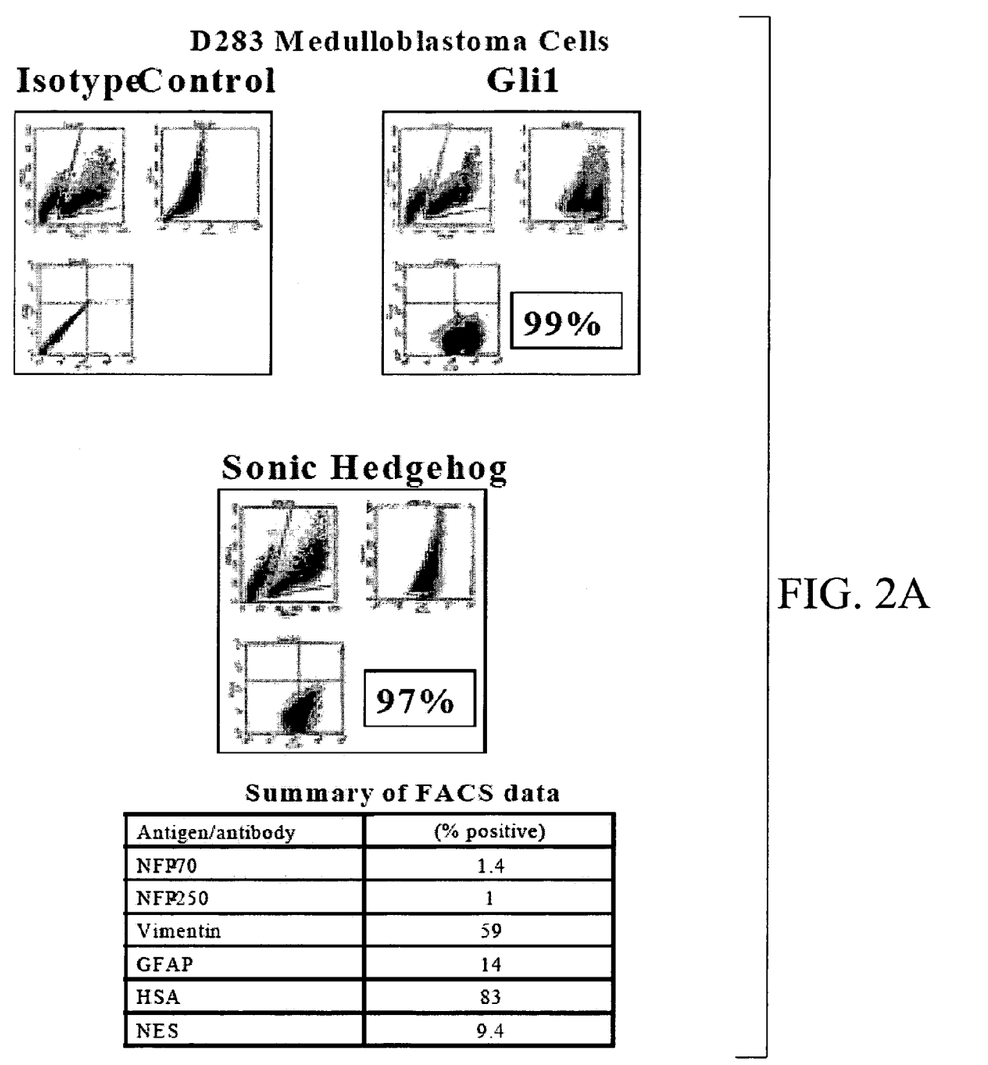
FIG. 2 is a series of histograms and a table showing expression of neural markers by tumor cells.
Figure 2B:
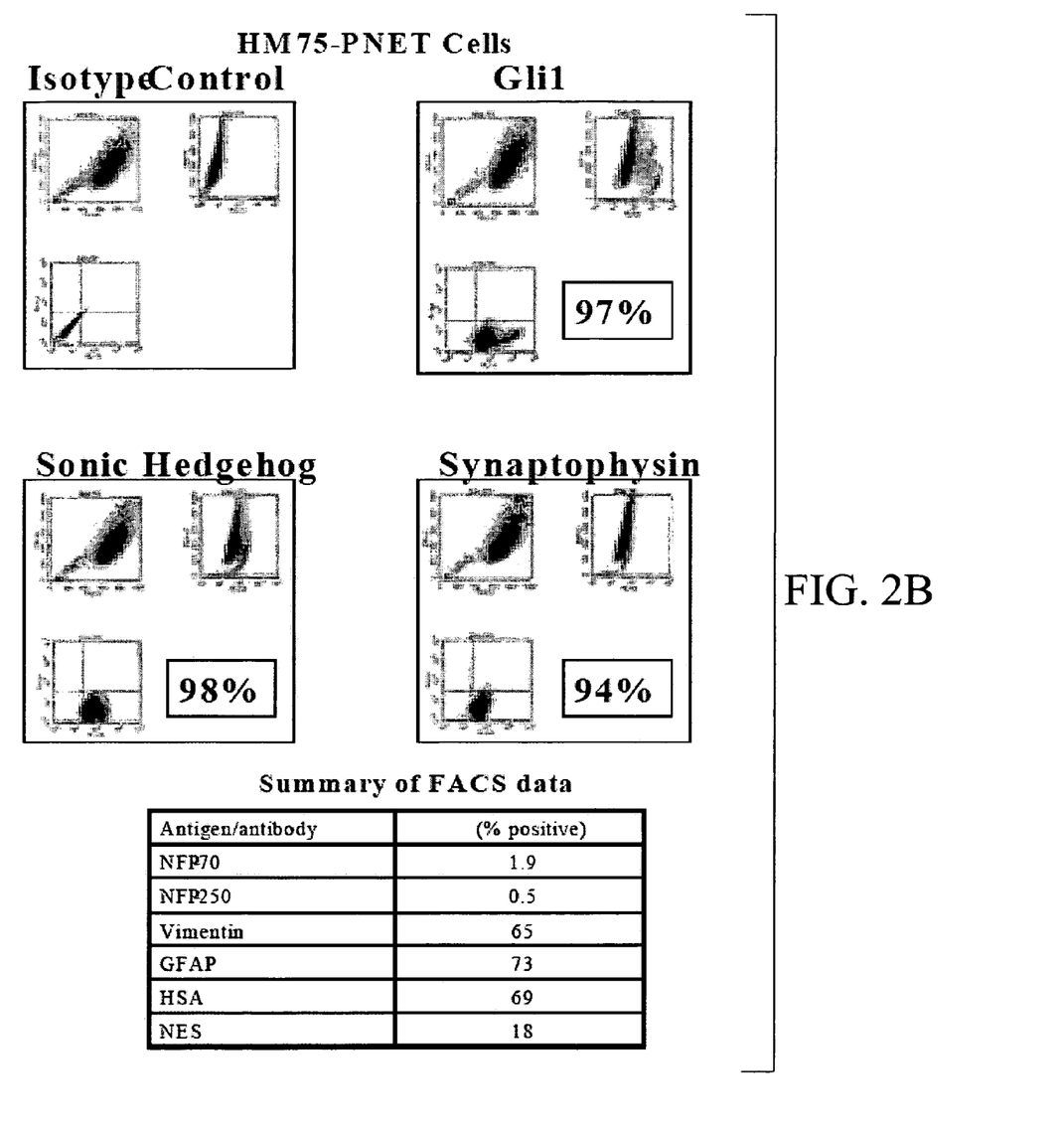

Phenotypic analysis of PNET cell cultures: To establish the primitive phenotype and neural origin of the PNET cell line D283 and cell line HM75, prior to gene targeting, indirect fluorescent antibody tagging was carried out using antibodies as described in table 1. To label intracellular antigens for both FACS analysis and IFA, the cells were subjected to a fixation and permeabilization procedure as previously described. Once labeled, the cells were analyzed on either a FACSCalibur four-color flow Cytometer or a UV microscope. The data summarized in Table I and FIGS. 1 & 2, show that both cell lines have similar phenotype, expressing most of the neural stem cell markers that were examined but do not express either of the neurofilament proteins (NFP-70 NFP-250) or glutamine synthetase (GS). For IFA, antibody-labeled cells were subjected to cyto-centrifugation (200 rpm for 5 minutes), air dried and placed under PBS-buffered glycerol and a coverslip. Cells were then examined using uv light microscopy and the degree of fluorescence determined and recorded as follows: 80%-100%=(4+); 50%-80%=(3+); 20%-50%=(2+); 5%-20%=(1+) and 0%-5%=(−). Also shown is the normal protein expression of both SHh and Gli1 in both the PNET tumor lines. FIGS. 2a and 2b give examples of the FACS analysis obtained in such experiments. The data suggest good correlation between the results obtained by indirect fluorescence and the Flow data. The representative data in FIGS. 2a and 2b shows that under normal cultural conditions both cell lines express significant amounts of both the SHh and Gli1 proteins. Both cell lines nearly 100% of the cells express these proteins. Interestingly, the tumor line, D283, has a small population of cells that exhibit significantly higher levels of SHh, the significance of which still needs to be determined. Either by flow analysis or by indirect fluorescent labeling, the phenotype of the PNET cell lines can be expressed as shown in Table 2.

Molecular Studies: From the antibody studies mentioned above, it appears that both the PNET cell line D283 and HM75 would be appropriate to use in the in vitro gene silencing studies. Both total RNA and mRNA have been isolated from the respective tumor line and stored at −80° C. However, only mRNA was used in the northern blot analysis.

Figure 3:
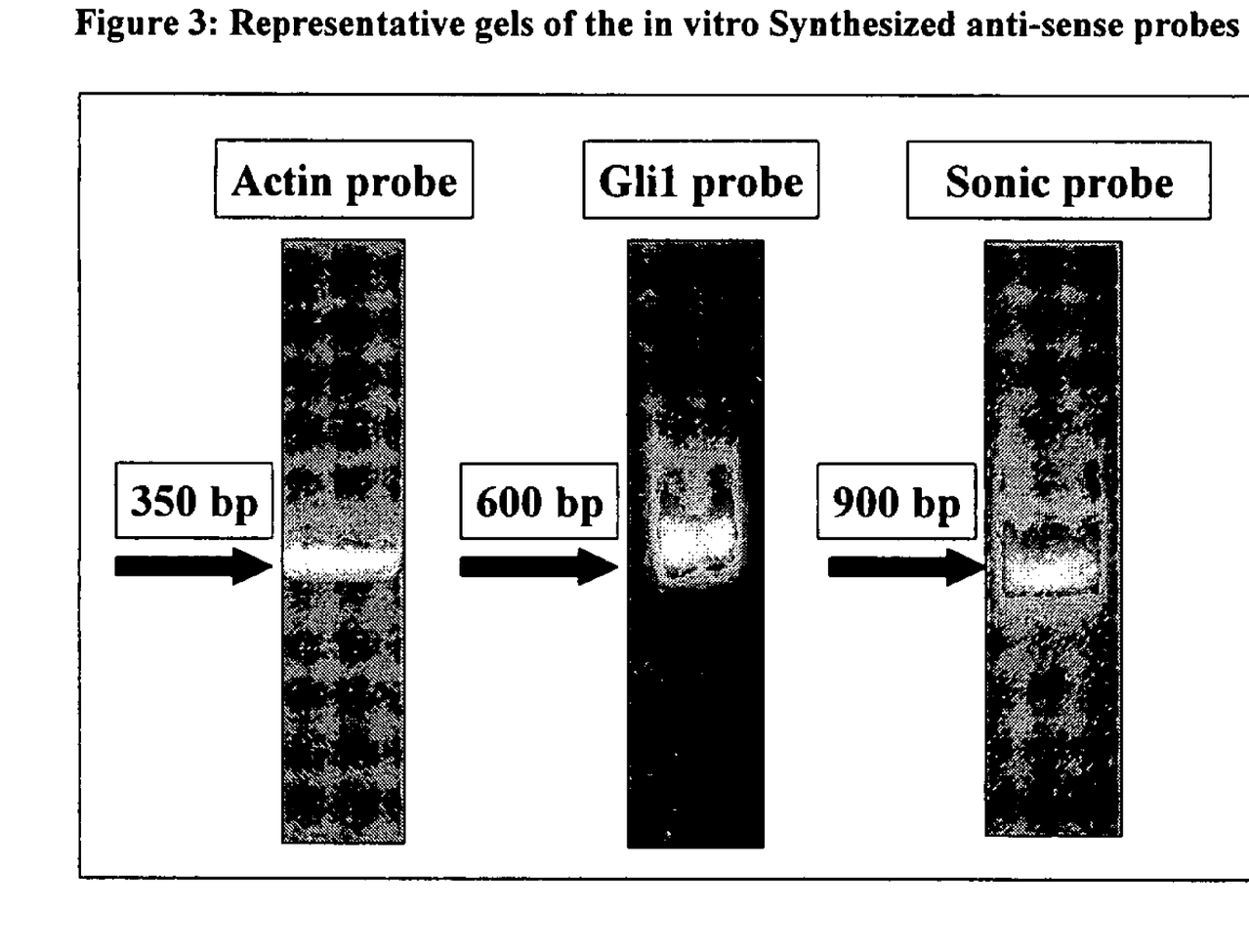
FIG. 3 is an illustration of the development of probes for a Northern blot analysis.

Synthesis of the probes for Northern blot analysis: The development of the probes used in this study is summarized in FIG. 3 (*a,b,c*). Briefly, A multi-purpose cloning vector (with an ampicillin resistant marker) also containing opposable T3 and T7 promotors that flanked a multiple cloning site were used to clone portions of the human shh and gli1 genes. The genes of interest were cloned into the vector at a NotI and EcoR1 cloning site. Competent bacteria containing the plasmid were grown as colonies on LB agar (containing 50 ug/ml of ampicillin). Individual colonies of bacteria were picked and placed in 5 ml of LB broth (supplemented with 50 ug/ml of ampicillin) and incubated overnight at 37° C. in an orbital shaker. From overnight cultures, plasmid preparations were carried out using Gibco BRL "CONCERT" mini-plasmid-prep system. 1% agarose gels were run to verify the purity of the plasmid preps (FIG. 3a). Restriction enzyme analysis (double digests using Not 1 and EcoR1) was also performed to verify the insert size (data not shown). βactin was the reporter gene that was used as control for the gene silencing experiments.

Northern hybridization was the method used to assay for levels of the target mRNA. RNA probes were chosen over DNA probes because they offer 10-fold better sensitivity and were synthesized by random priming using Strip-EZ RNA Kit. Purified plasmid preps were linearized downstream of the insert with EcoR1. This allowed us to transcribe the antisense RNA probe using the T3 RNA polymerase. Following the removal of the DNA template (linearized plasmid), the RNA probes were purified, concentrated by precipitation and stored at −75° C. (FIG. 3b).

Because the RNA was synthesized using the Strip-EZ RNA Kit, the probes were labeled post synthesis with Psoralen-Biotin. Furthermore, the use of modified CTP in the transcription and synthesis of the antisense RNA probe allows us to degrade and strip the hybridized probe from the northern blots for re-use is subsequent experiments. FIG. 3c shown below is an example of a test blot at varying concentrations showing both the shh and gli probe activities.

Figure 4A:
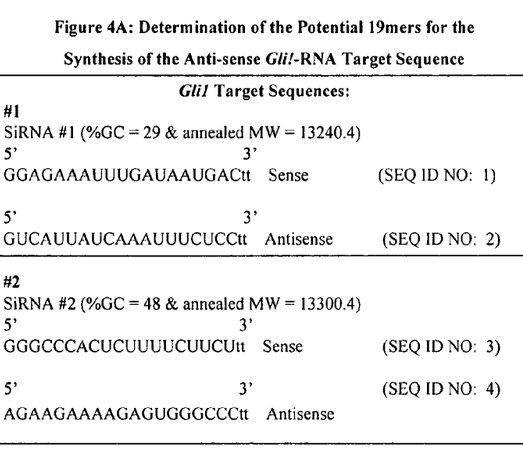
FIG. 4 is a series of tables showing the determination of the potential 19mer for the synthesis of anti-sense RNA target sequences.
Figure 4B:
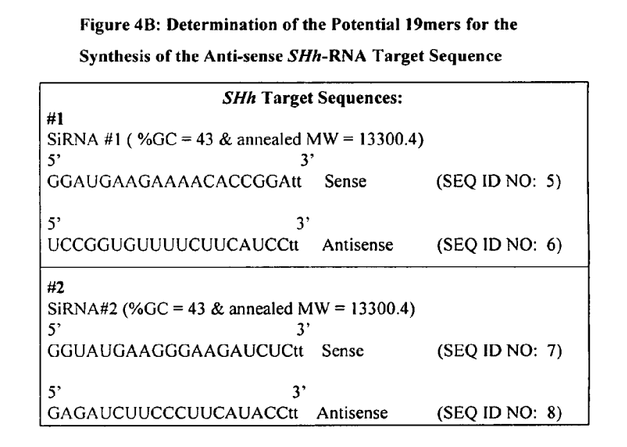
Figure 4C:
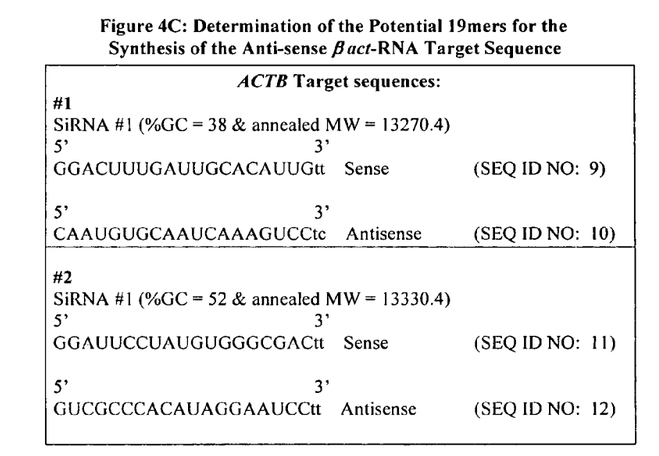

Determination of the gene sequences for the synthesis of the 19mer antisense RNAi's: SiRNAs were constructed for the genes encoding shh and gli1 and β actin. The coding sequences and the transcript sequences were taken from the data given in the Ensembl Human and Murine Gene Bank (The Wellcome Trust, Sanger Institute). In this study, the identification of siRNA target sites were determined as stated in the experimental methods section. Two SiRNA sequences per target were designed for each of the genes under study (see FIGS. 4a,b and c), an SiRNA containing a 'scrambled' sequence was synthesized to serve as a negative control.

Figure 5:
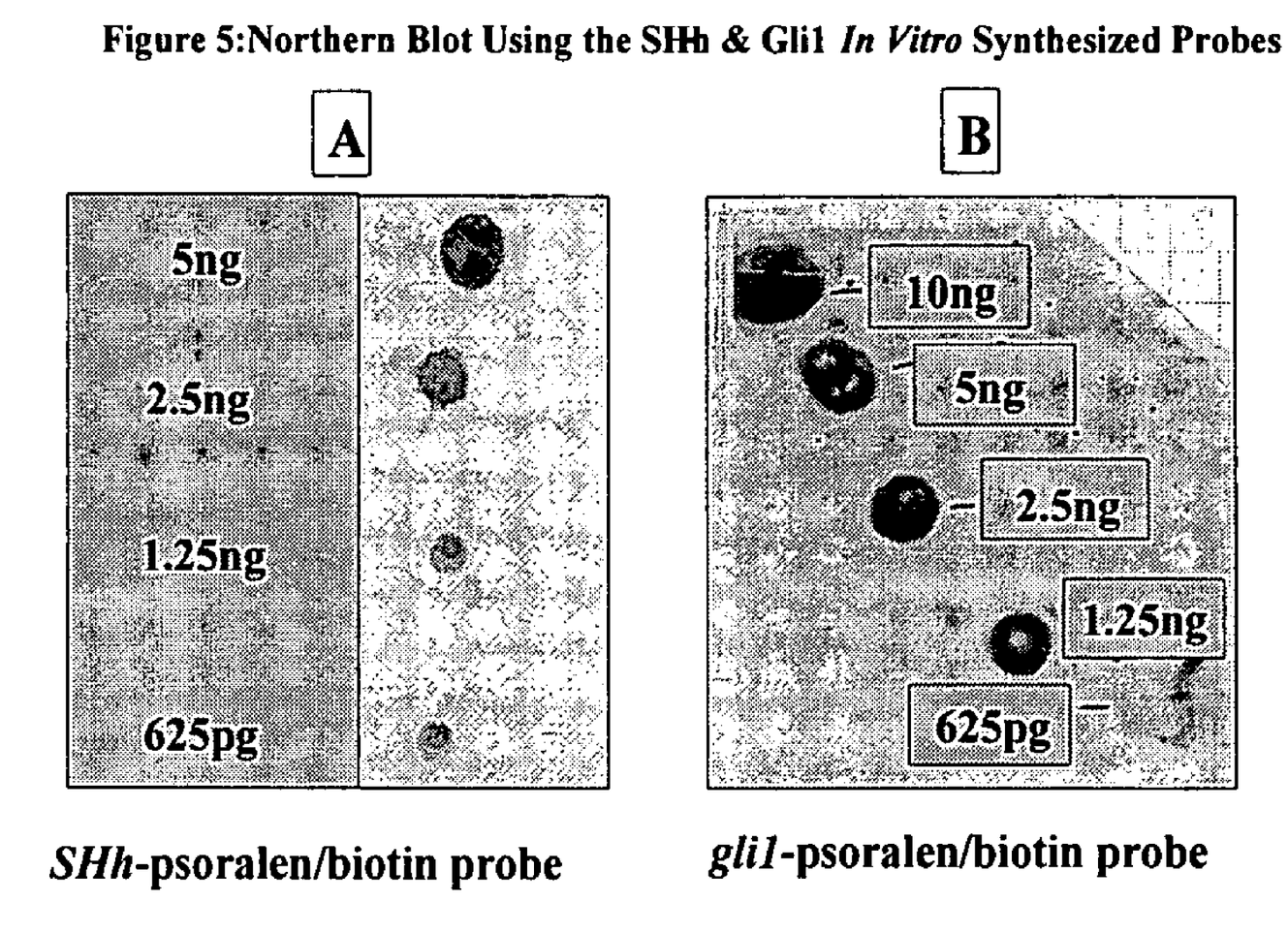
FIG. 5 is a Northern blot analysis of PNET tumor cells treated with different protocols.
Figure 6A:
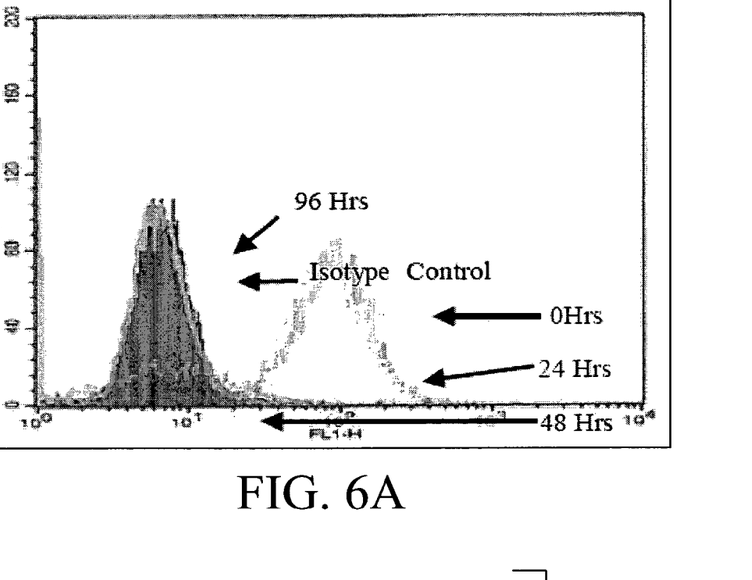
FIG. 6 is a flow cytometric analysis of PNET tumor cells treated with different protocols.
Figure 6B:
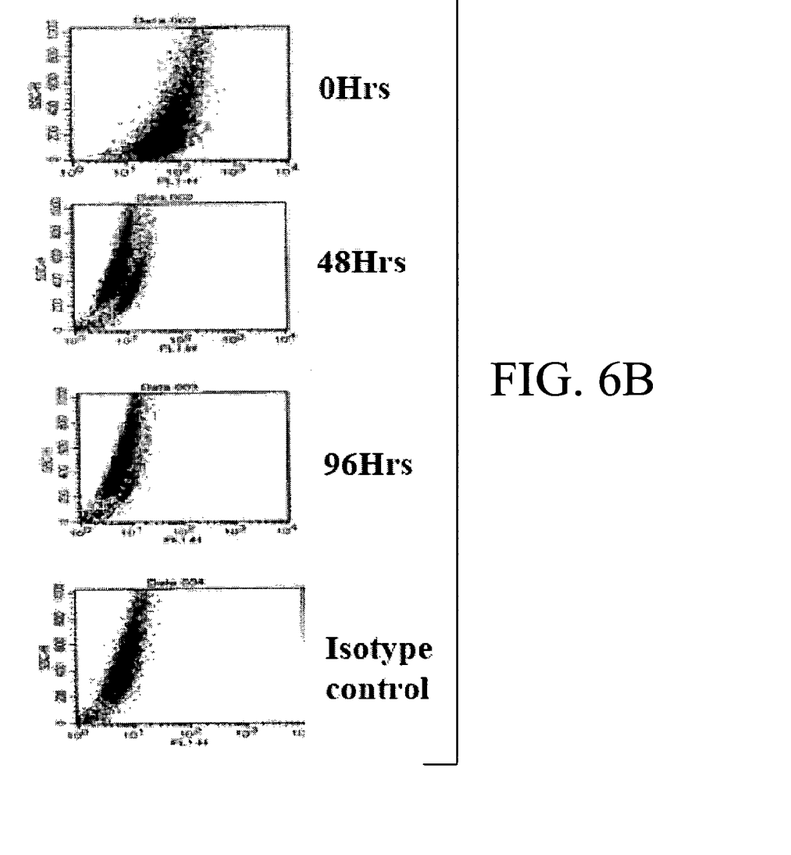
Figure 7:
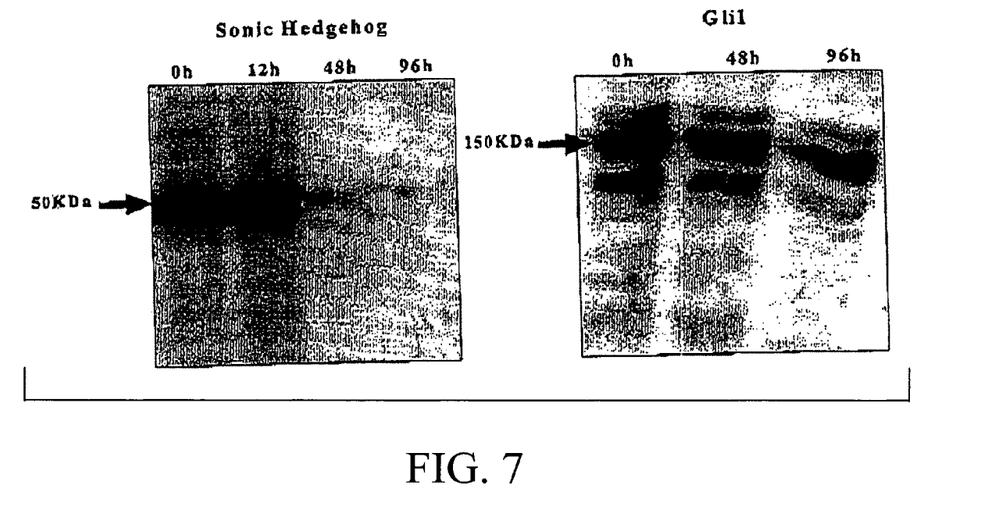
FIG. 7 is a Western blot of PNET tumor cells treated with different protocols.
Figure 8:
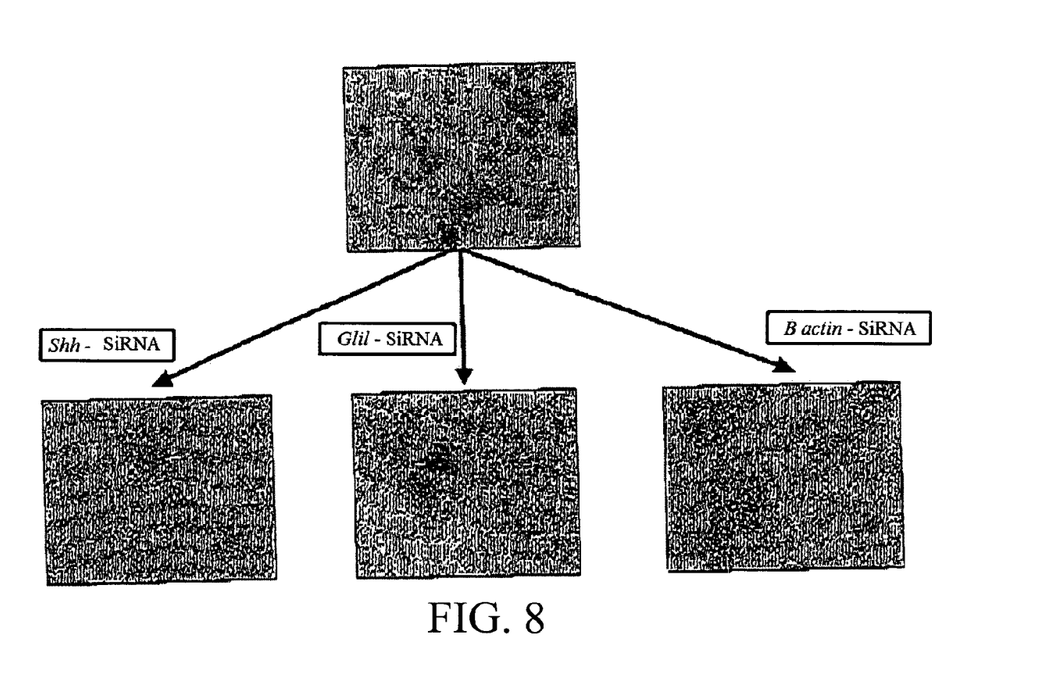
FIG. 8 is a series of photomicrographs of PNET tumor cells treated with different protocols.

Characterization of the siRNA induced gene silencing of targeted genes: To test the protocol and the synthesized SiRNAs, the Shh and gli1-specific SiRNAs were transfected using siPort™ Lipid. The mRNA was obtained prior to the SiRNA treatment and at 12, 24, 48 and 96 hours following treatment. Northern blot analysis of cells treated with the SiRNAs (see FIG. 5) indicated that the level of mRNA specific for either of the targeted genes (Shh and gli1) was significantly reduced within 24 hours and under experimental conditions used in this study was not detectable at 96 hours following SiRNA treatment. Treatment of the cells with either of the shh or gli1 SiRNAs did not effect the level of β actin-specific mRNA (FIG. 5). To assess the effect on protein expression treated cells were examined by IFA (Table 3), western blot analysis and flow cytometry. FIGS. 6a & 6b show the loss of protein expression in the PNET cells following the shh-SiRNA treatment. As with the mRNA levels protein expression was reduced significantly and by 96 hours no detectable protein was observed. The western blot analysis (FIG. 7) of the treated cells also shows significant reduction of the protein expression such that in the shh-treated cells protein was barely detectable by 96 hours post treatment. In the gli1-treated cells a reduction in protein expression was observed but there was significantly more gli1 expression by 96 hours when compared to the shh-treated cells. Cells that were treated with the siRNAs were re-plated in 12-well plates and incubated at 37° C. and observed for in vitro growth characteristics. The only significant change in the growth of the cells is shown in FIG. 8. Under normal cell growth these cells were predominantly non-adherent proliferating in clusters in the supernatant. Following siRNA-treatment the cells were predominantly adherent and had a significantly slower growth rate. This change was more visible in those cells that were treated with the shh siRNA than those treated with gli1-siRNA.

OTHER EMBODIMENTS

While the above description contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

What is claimed is:

1. A method for inhibiting expression of SHh in primitive neuroectodermal (PNET) tumor cells, comprising transfecting the tumor cells with an effective amount of a siRNA primer pair consisting of the antisense shh gene sequences SEQ ID NO:6 and SEQ ID NO:8 wherein the transfected tumor cells change from non-adherent proliferating cells to adherent proliferating cells after transfecting in vitro thereby altering growth, phenotype and growth characteristics of the adherent proliferating cells.

2. The method of claim 1 wherein the PNET tumor cell is selected from the group consisting of medulloblastoma, basal cell carcinoma, fibroma, meningioma, and rhabdomyosarcoma.

3. The method of claim 1 wherein the PNET tumor cell is a D283 cell.

4. The method of claim 1 wherein inhibiting expression of the shh gene decreases-protein expression by up to about 85% compared to normal protein expression in the tumor cells.

5. The method of claim 1 wherein the transfected tumor cells exhibit reduced growth in vitro compared to untransfected tumor cells.

* * * * *

UNITED STATES PATENT AND TRADEMARK OFFICE
CERTIFICATE OF CORRECTION

| | | |
|---|---|---|
| PATENT NO. | : 7,666,676 B2 | Page 1 of 1 |
| APPLICATION NO. | : 11/436962 | |
| DATED | : February 23, 2010 | |
| INVENTOR(S) | : Michael Lawman and Selena Braccili | |

It is certified that error appears in the above-identified patent and that said Letters Patent is hereby corrected as shown below:

Column 2,
Line 64, "FIG. 1 is series" should read --FIG. 1 is a series--.

Column 3,
Line 33, "(% GC 43" should read --(% GC=43--.

Column 4,
Line 30, "Gli1antigens" should read --Gli1 antigens--.
Line 44, "cells sec-$^1$" should read --cells sec-$^1$.--.

Column 5,
Line 53, "200 μof Water" should read --200 μl of Water--.

Column 12,
Line 55, "decreases-protein" should read --decreases protein--.

Signed and Sealed this

Eighteenth Day of May, 2010

David J. Kappos
*Director of the United States Patent and Trademark Office*

SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Gli1 Target Sequence #1, sense, SiRNA #1 (%GC = 29 & annealed MW = 13240.4)

<400> SEQUENCE: 1
ggagaaauuu gauaaugact t                                              21

<210> SEQ ID NO 2
<211> LENGTH: 21
<212> TYPE: DNA
<213> ORGANISM: Artificial Sequence
<220> FEATURE:
<223> OTHER INFORMATION: Gli1 Target Sequence #1, antisense, SiRNA #1
      (%GC = 29 & annealed MW = 13240.4)

-continued

<400> SEQUENCE: 2
gucauuauca aauuucucct t                                              21

<210> SEQ ID NO 3
<211> LENGTH: 21
<212> TYPE: DNA
<213> ORGANISM: Artificial Sequence
<220> FEATURE:
<223> OTHER INFORMATION: Gli1 Target Sequence #2, sense, SiRNA #2 (%GC =
      48 & annealed MW = 13300.4)

<400> SEQUENCE: 3
gggcccacuc uuuucuucut t                                              21

<210> SEQ ID NO 4
<211> LENGTH: 21
<212> TYPE: DNA
<213> ORGANISM: Artificial Sequence
<220> FEATURE:
<223> OTHER INFORMATION: Gli1 Target Sequence #2, antisense, SiRNA #2
      (%GC = 48 & annealed MW = 13300.4)

<400> SEQUENCE: 4
agaagaaaag agugggccct t                                              21

<210> SEQ ID NO 5
<211> LENGTH: 21
<212> TYPE: DNA
<213> ORGANISM: Artificial Sequence
<220> FEATURE:
<223> OTHER INFORMATION: SHh Target Sequence #1, sense, SiRNA #1 (%GC =
      43 & annealed MW = 13300.4)

<400> SEQUENCE: 5
ggaugaagaa aacaccggat t                                              21

<210> SEQ ID NO 6
<211> LENGTH: 21
<212> TYPE: DNA
<213> ORGANISM: Artificial Sequence
<220> FEATURE:
<223> OTHER INFORMATION: SHh Target Sequence #1, antisense, SiRNA #1
      (%GC = 43 & annealed MW = 13300.4)

<400> SEQUENCE: 6
uccgguguuu ucuucaucct t                                              21

<210> SEQ ID NO 7
<211> LENGTH: 21
<212> TYPE: DNA
<213> ORGANISM: Artificial Sequence
<220> FEATURE:
<223> OTHER INFORMATION: SHh Target Sequence #2, sense, SiRNA#2 (%GC =
      43 & annealed MW = 13300.4)

<400> SEQUENCE: 7
gguaugaagg gaagaucuct t                                              21

<210> SEQ ID NO 8
<211> LENGTH: 21
<212> TYPE: DNA
<213> ORGANISM: Artificial Sequence
<220> FEATURE:
<223> OTHER INFORMATION: SHh Target Sequence #2, antisense, SiRNA#2
      (%GC = 43 & annealed MW = 13300.4)

<400> SEQUENCE: 8

```
gagaucuucc cuucauacct t                                              21

<210> SEQ ID NO 9
<211> LENGTH: 21
<212> TYPE: DNA
<213> ORGANISM: Artificial Sequence
<220> FEATURE:
<223> OTHER INFORMATION: ACTB Target sequence #1, sense, SiRNA #1 (%GC =
      38 & annealed MW = 13270.4)

<400> SEQUENCE: 9
ggacuuugau ugcacauugt t                                              21

<210> SEQ ID NO 10
<211> LENGTH: 21
<212> TYPE: DNA
<213> ORGANISM: Artificial Sequence
<220> FEATURE:
<223> OTHER INFORMATION: ACTB Target sequence #1, antisense, SiRNA #1
      (%GC = 38 & annealed MW = 13270.4)

<400> SEQUENCE: 10
caaugugcaa ucaaagucct c                                              21

<210> SEQ ID NO 11
<211> LENGTH: 21
<212> TYPE: DNA
<213> ORGANISM: Artificial Sequence
<220> FEATURE:
<223> OTHER INFORMATION: ACTB Target sequence #2, sense, SiRNA #1 (%GC =
      52 & annealed MW = 13330.4)

<400> SEQUENCE: 11 ggauccuau gugggcgact t                                               21

<210> SEQ ID NO 12
<211> LENGTH: 21
<212> TYPE: DNA
<213> ORGANISM: Artificial Sequence
<220> FEATURE:
<223> OTHER INFORMATION: ACTB Target sequence #2, antisense, SiRNA #1
      (%GC = 52 & annealed MW = 13330.4)

<400> SEQUENCE: 12
gucgcccaca uaggaaucct t                                              21
```